(12) United States Patent
Goldberg

(10) Patent No.: US 6,860,122 B2
(45) Date of Patent: Mar. 1, 2005

(54) FABRIC WITH PAIN-RELIEVING CHARACTERISTICS AND STRUCTURES THEREFROM, AND METHOD

(75) Inventor: Arthur Goldberg, Livingston, NJ (US)

(73) Assignee: F&S, LLC, Englewood, NJ (US)

( * ) Notice: Subject to any disclaimer, the term of this patent is extended or adjusted under 35 U.S.C. 154(b) by 411 days.

(21) Appl. No.: 10/109,177

(22) Filed: Mar. 28, 2002

(65) Prior Publication Data

US 2003/0186607 A1 Oct. 2, 2003

(51) Int. Cl.$^7$ .............................................. D04B 1/14
(52) U.S. Cl. ...................................................... 66/202
(58) Field of Search .......................... 607/2, 3, 46, 144, 607/145, 149, 152; 66/190–195, 202; 442/313, 308

(56) References Cited

U.S. PATENT DOCUMENTS

| 2,670,620 A | * | 3/1954 | Goldstaub ..................... 66/195 |
| 4,753,088 A | | 6/1988 | Harrison et al. |
| 4,815,299 A | | 3/1989 | Bryant |
| 4,856,299 A | | 8/1989 | Bryant |
| 4,878,148 A | * | 10/1989 | Hee ............................. 66/193 |
| 4,921,751 A | * | 5/1990 | Wakahara et al. ............ 66/202 |
| 6,014,585 A | | 1/2000 | Stoddard |
| 6,291,375 B1 | * | 9/2001 | Allen et al. .................... 66/202 |

FOREIGN PATENT DOCUMENTS

| EP | 0 997 565 A2 | 5/2000 |
| JP | 05944740 | 8/1999 |
| WO | PCT 09915101 | 4/1999 |

OTHER PUBLICATIONS

Lifestyle Fascination, Inc.; Revolutionary carbon wraps soothe pain with heat on . . . ; www.shoplifestyle.com; Feb. 4, 2002; Lakewood, New Jersey, United States.

* cited by examiner

Primary Examiner—Danny Worrell
(74) Attorney, Agent, or Firm—Summa & Allan, P.A.

(57) ABSTRACT

A fabric for reducing endogenous pain by application of the fabric to a pain site to facilitate the flow of endogenous electrical current in the body, and including a knitted stretch fabric having a knit base structure of electrically non-conductive fibers forming courses and wales, a first electrically-conductive carbon fiber knitted into and extending along first selected wales and transversely along first selected courses of the base structure, and a second electrically-conductive carbon fiber knitted into and extending along second selected wales and transversely along second selected courses of the base structure intersecting the first selected courses for contacting the first electrically-conductive carbon fiber and thereby defining a matrix of first and second electrically-conductive carbon fibers that induce an electrical current in the presence of an electrical charge.

7 Claims, 4 Drawing Sheets

FABRIC WITH PAIN-RELIEVING CHARACTERISTICS AND STRUCTURES THEREFROM, AND METHOD

TECHNICAL FIELD AND BACKGROUND OF THE INVENTION

This invention relates to a fabric with pain-relieving characteristics, structures such as garments and bandages constructed therefrom, and related methods. The fabric is similar to prior art fabrics which are known and have been used for dissipating static electricity in products such as surgical drapes. It has been observed that by incorporating two different types of electrically-conductive carbon fibers into a non-conductive base, and structuring the fabric in such a way that the two electrically-conductive fibers touch each other to form a matrix, an electric current can be induced of sufficient magnitude to generate a current flow.

It is also known that some forms of pain is accompanied by an increase in resistance to endogenous electrical flow arising from interrupted, damaged or compressed cells. This is discussed in U.S. Pat. No. 6,014,585, particularly at cols. 1 and 2. This patent discloses the use of an ion-conducting tape which is stuck to the body at the pain site. Other patents cited within the '585 Patent disclose other various methods of pain reduction.

Endogenous electrical flow within the body, that is, electrical flow within the body originating from the organism itself, can therefore be stimulated. The inventor has observed as a result of a pain-inducing household accident while holding a piece of knitted fabric according to a particular construction that application of the fabric to the pain site can result in immediate, total relief from the pain. No representation is made that any cure occurs, or that any palliative effect results which lasts after removal of the fabric.

SUMMARY OF THE INVENTION

Therefore, it is an object of the invention to provide a fabric which relieves pain when applied to and maintained on the site.

It is another object of the invention to provide a fabric which uses carbon fibers to form a matrix which conducts endogenous electricity.

It is another object of the invention to provide a knitted fabric which can be constructed into structures which can be applied to and maintained on a pain site to relieve pain.

It is another object of the invention to provide a method of constructing a fabric which can be used to construct garments and medical products which can be placed and held against a pain site.

These and other objects of the present invention are achieved in the preferred embodiments disclosed below by providing a fabric for reducing endogenous pain by application of the fabric to a pain site to facilitate the flow of endogenous electrical current in the body, and comprising a knitted stretch fabric comprised of a knit base structure of electrically non-conductive fibers forming courses and wales, a first electrically-conductive carbon fiber knitted into and extending along first selected wales and transversely along first selected courses of the base structure, and a second electrically-conductive carbon fiber knitted into and extending along second selected wales and transversely along second selected courses of the base structure intersecting the first selected courses for contacting the first electrically-conductive carbon fiber and thereby defining a matrix of first and second electrically-conductive carbon fibers that induce an electrical current in the presence of an electrical charge.

According to one preferred embodiment of the invention, the first electrically-conductive carbon fiber is chosen from the group consisting of carbon suffused nylon, filamentary polymer substrates having finely divided, electrically conductive particles embossed on the surface of the surface of the polymer, a core of electrically-conductive carbon surrounded by a electrically non-conductive polymercover, and graphite fibers, and the second electrically-conductive carbon fiber is chosen from the group consisting of carbon suffused nylon, filamentary polymer substrates having finely divided, electrically conductive particles embossed on the surface of the surface of the polymer, a core of electrically-conductive carbon surrounded by a electrically non-conductive polymer cover, and graphite fibers, but exclusive of the carbon fiber comprising the first electrically-conductive fiber.

According to another preferred embodiment of the invention, the first electrically-conductive carbon fiber comprises a carbon suffused nylon and the second electrically-conductive carbon fiber comprises a core of electrically-conductive carbon surrounded by a electrically non-conductive polymer cover.

According to yet another preferred embodiment of the invention, the matrix contacts both the technical face and technical back of the fabric.

According to yet another preferred embodiment of the invention, a fabric is provided for reducing endogenous pain by application of the fabric to a pain site to facilitate the flow of endogenous electrical current in the body. The fabric comprises a 3-bar warp-knitted stretch fabric comprised of a knit base structure of stretch nylon forming courses and wales, a carbon suffused nylon fiber knitted into and extending along first selected wales and transversely along first selected courses of the base structure, and a fiber having a core of electrically-conductive carbon surrounded by a electrically non-conductive polymer cover knitted into and extending along second selected wales and transversely along second selected courses of the base structure intersecting the first selected courses for contacting the carbon suffused nylon and thereby defining a matrix of first and second electrically-conductive carbon fibers contacting both the technical front face and technical back face and that induce an electrical current in the presence of an electrical charge. The fabric is stitched according to the construction:

Top bar—stretch nylon knitting a double needle underlap stitch (2-0, 1-3);

Middle bar—6 ends out and one end in of the fiber having a core of electrically-conductive carbon surrounded by a electrically non-conductive polymer cover stitched according to the sequence:

(8-9, 8-7)x4, (1-0, 1-2)x4, with an intermediate let off pattern chain for the middle bar having a ratio of 1.21 of (O)x1, (4)x23, (O)x1, (4)x23;

Bottom bar—6 ends out and one end in of the carbon suffused nylon fiber according to the sequence:

(1-0, 1-2)×4, (8-9, 8-7)×4, with an intermediate let off pattern chain for the middle bar having a ratio of 1.21 of (O)×1, (4)×23, (O)×1, (4)×23.

According to yet another preferred embodiment of the invention, the fabric comprises a garment.

According to yet another preferred embodiment of the invention, the garment comprises a glove.

According to yet another preferred embodiment of the invention, the fabric is incorporated into a bandage.

According to yet another preferred embodiment of the invention, the bandage includes a strap for retaining the pad on a predetermined desired part of the body to be treated for pain.

According to yet another preferred embodiment of the invention, a fabric is provided for reducing endogenous pain by application of the fabric to a pain site to facilitate the flow of endogenous electrical current in the body. The fabric comprises a fabric comprised of a base structure of electrically non-conductive fibers, a first electrically-conductive carbon fiber integrated into and extending in a first direction along the fabric and transversely in a second direction along the fabric; and a second electrically-conductive carbon fiber integrated into and extending along a length of the transversely to at least one direction of the first fiber along the fabric for contacting the first electrically-conductive carbon fiber and thereby defining a matrix of first and second electrically-conductive carbon fibers that induce an electrical current in the presence of an electrical charge.

An embodiment of the method of reducing endogenous pain by stimulating a flow of endogenous electrical current in the body according to the invention comprises the steps of knitting a stretch fabric comprised of a knit base structure of electrically non-conductive fibers forming courses and wales, a first electrically-conductive carbon fiber knitted into and extending along first selected wales and transversely along first selected courses of the base structure, and a second electrically-conductive carbon fiber knitted into and extending along second selected wales and transversely along second selected courses of the base structure intersecting the first selected courses for contacting the first electrically-conductive carbon fiber and thereby defining a matrix of first and second electrically-conductive carbon fibers that induce an electrical current in the presence of an electrical charge. The fabric is applied to a pain site, and the fabric is maintained on the pain site for the duration of desired relief.

According to yet another preferred embodiment of the invention, the first electrically-conductive carbon fiber is chosen from the group consisting of carbon suffused nylon, filamentary polymer substrates having finely divided, electrically conductive particles embossed on the surface of the surface of the polymer, a core of electrically-conductive carbon surrounded by a electrically non-conductive polymercover, and graphite fibers, and the second electrically-conductive carbon fiber is chosen from the group consisting of carbon suffused nylon, filamentary polymer substrates having finely divided, electrically conductive particles embossed on the surface of the surface of the polymer, a core of electrically-conductive carbon surrounded by a electrically non-conductive polymer cover, and graphite fibers, but exclusive of the carbon fiber comprising the first electrically-conductive fiber.

According to yet another preferred embodiment of the invention, the first electrically-conductive carbon fiber comprises a carbon suffused nylon and the second electrically-conductive carbon fiber comprises a core of electrically-conductive carbon surrounded by a electrically non-conductive polymer cover.

According to yet another preferred embodiment of the invention, the matrix contacts both the technical face and technical back of the fabric.

According to yet another preferred embodiment of the invention, the method includes the step of fabricating the fabric into a structure selected from the group consisting of garments and bandages.

According to yet another preferred embodiment of the invention, the step of fabricating the fabric comprises the step of fabricating a splint.

According to yet another preferred embodiment of the invention, the step of fabricating the fabric comprises the step of fabricating a glove.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
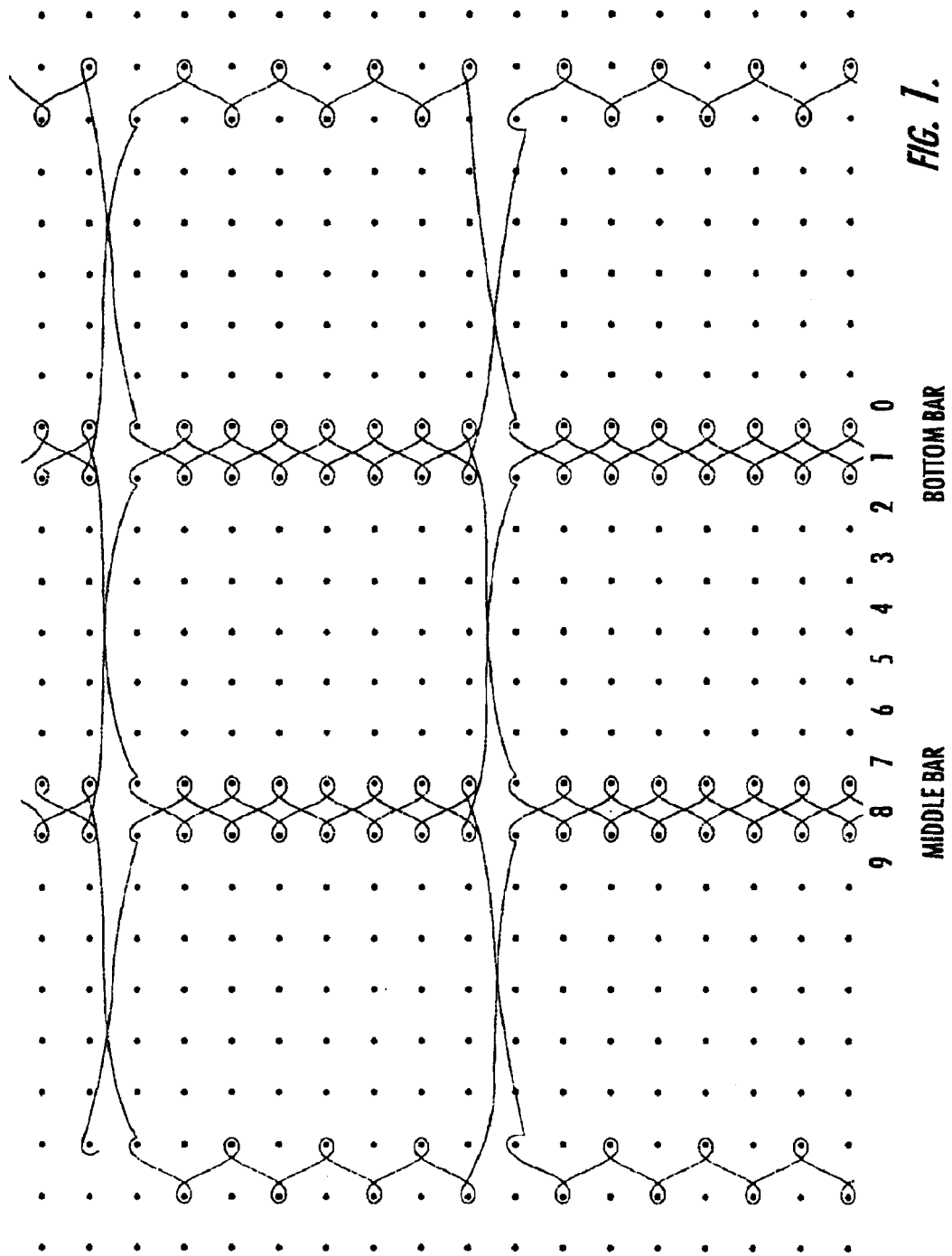
FIG. 1 is a stitch diagram of the electrically-conductive fiber stitches.
Figure 2:
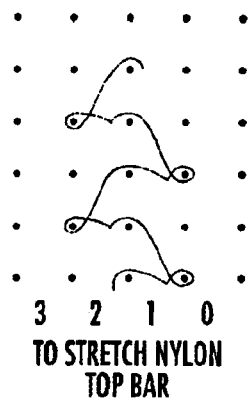
FIG. 2 is a stitch diagram of the non-electrically-conductive fiber stitches.

Referring now specifically to the drawings, a warp knit fabric according to the present invention is illustrated in FIGS. 1 and 2. This warp knit fabric may be formed on any suitable warp knit machine, such as a Mayer KE-3, 3 bar machine. Alternatively, a woven, circular or flat-knitted fabric may be formed incorporating the principles of the invention, including the provision of two distinct electrically-conductive carbon fiber components which have points of contact defining a matrix of fibers held in place by a base of non electrically-conductive fibers.

It has been found that such a fabric, when placed on a pain site, induces a endogenous flow of current sufficient to reduce or eliminate pain at the site while the fabric is in place on the pain site. Current flows in both the walewise and coursewise direction of the fabric.

One method of achieving this result is simply to apply the fabric to the pain site and hold it in place. However, incorporation into other structures will enhance the utility of the fabric and the pain relief achieved by enabling the fabric to be held in place while the wearer goes about daily life. In its simplest form, a length of the fabric may be wrapped around the area of the body where the pain site is located and held in place by tucking the end of the fabric under a wrap of the fabric, with a safety pin, or clip of the type used for holding wrap-type bandages in place.

Figure 3:
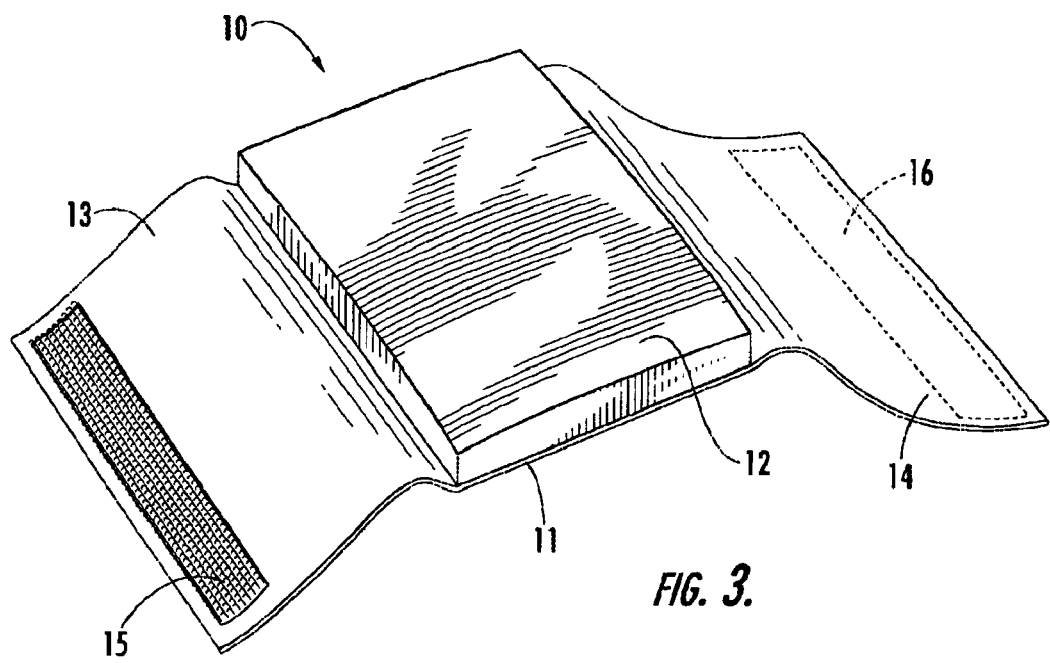
FIG. 3 is pad incorporating a fabric according to a preferred embodiment of the invention.

In addition, as is shown in FIG. 3, a pad 10 of any suitable size and shape may be constructed for being applied to and held on the pain site. The pad 10 is constructed of a fabric 11 according to a preferred embodiment of the invention applied by adhesive, sewing stitches, thermobonding or other suitable means to a padding material 12. A pair of opposed straps 13 and 14 with complementary hook and loop fastener elements 15 and 16, respectively, permit the pad 10 to encircle a limb or other body area and remain in place as long as desired.

Figure 4:
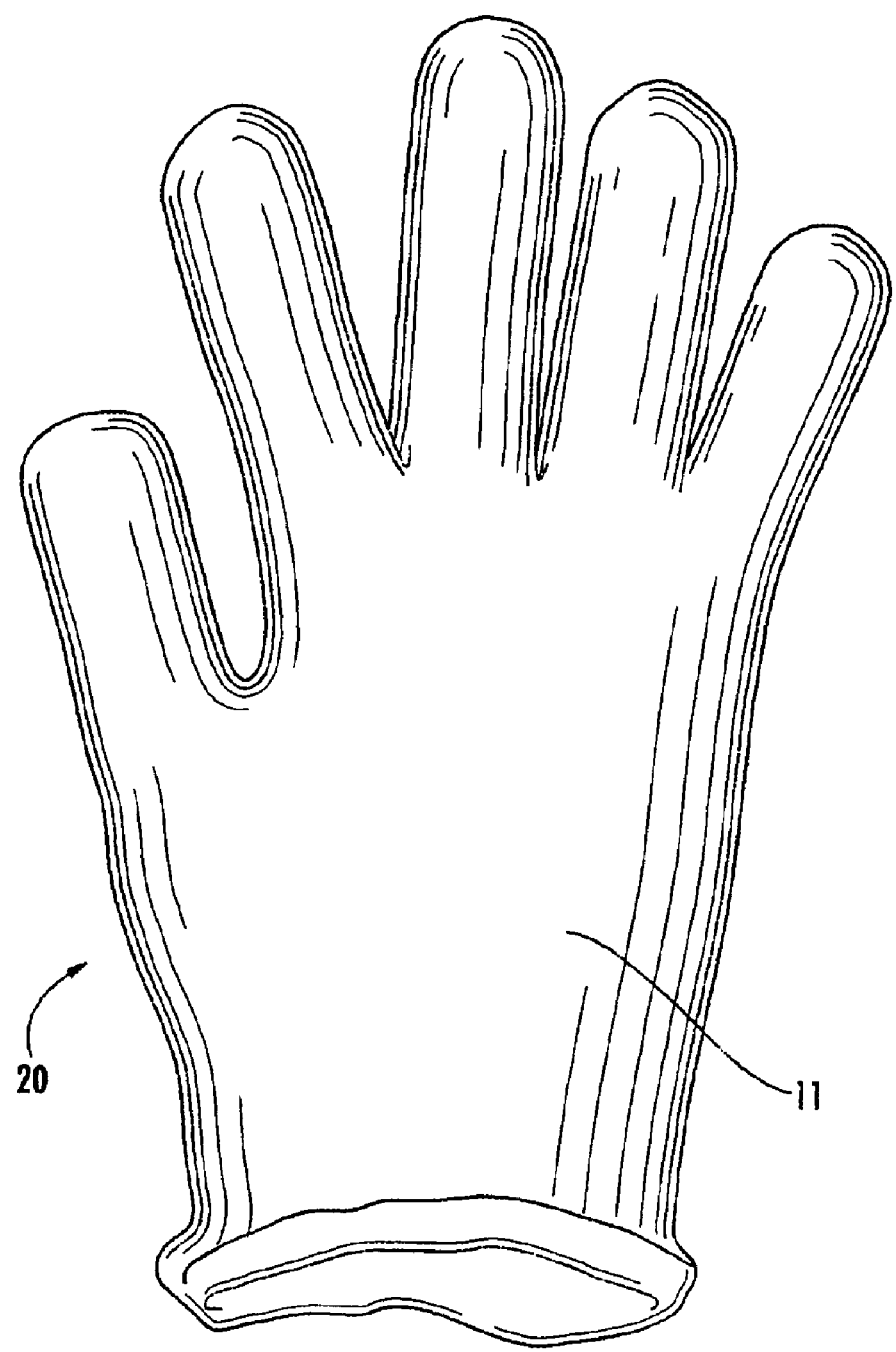
FIG. 4 is a glove constructed of a fabric according to a preferred embodiment of the invention.

As is shown in FIG. 4, the fabric 11 may be formed by cutting and sewing the fabric into a glove 20. The glove 20 may then be worn on the hand to relieve pain in the hand. Given the flexibility of the fabric 11 resulting from the use of stretch yarn, as described below, the glove 20 may preferably be fabricated so that it can be worn on either hand.

Figure 5:
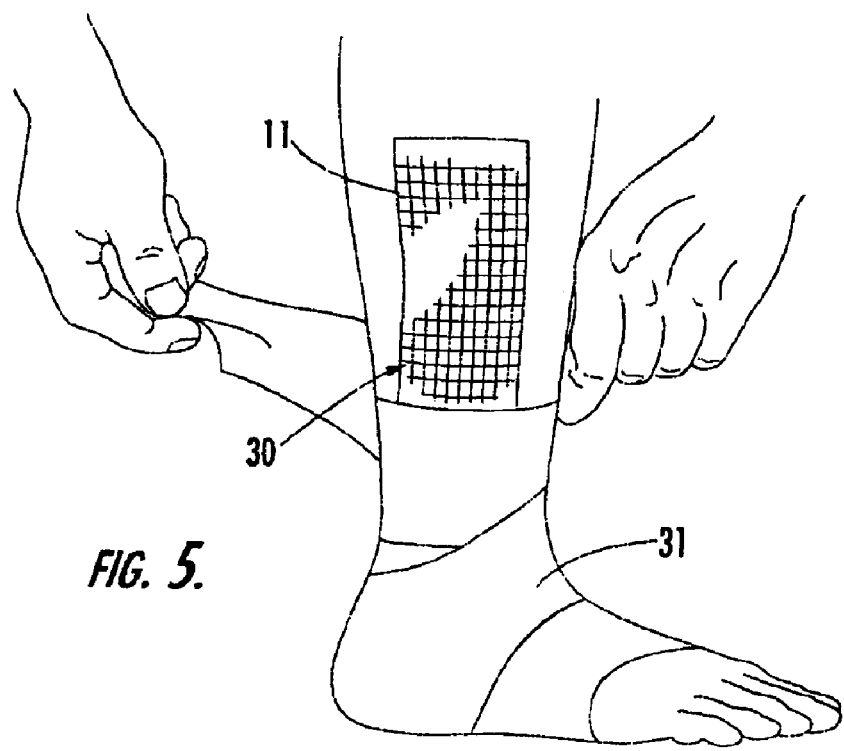
FIGS. 5 and 6 are a bandage in the form of a splint which incorporates a fabric covering in accordance with a preferred embodiment of the invention.
Figure 6:
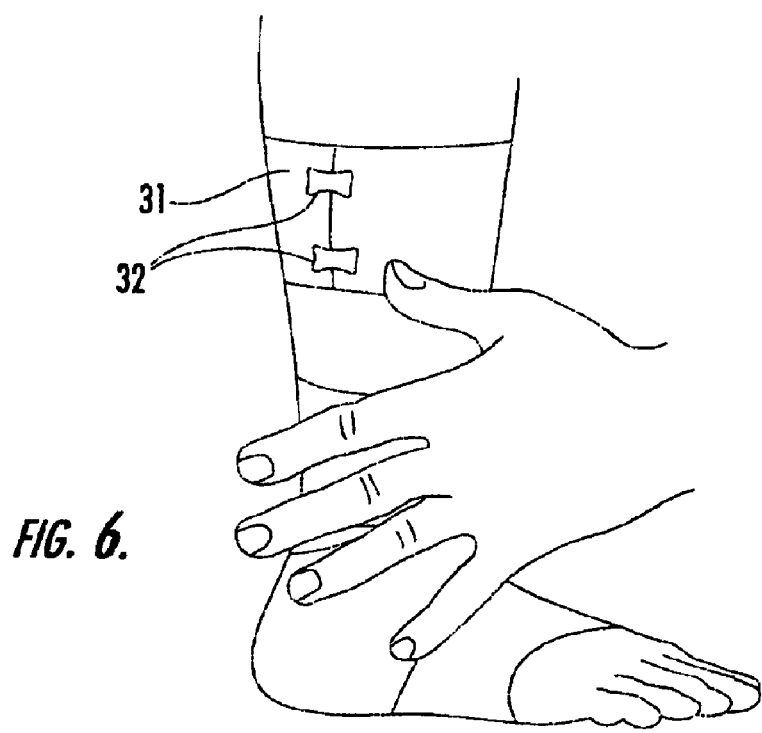

Referring to FIGS. 5 and 6, a bandage such as a splint 30 can be covered at least on the skin side of the splint 30 with a layer of fabric 11 in order to directly contact the skin. The fabric 11 is thereby held against the pain site along with the splint 30 by an overwrap of an elastic bandage 31 and retained in a suitably tensioned condition by clips 32, as particularly shown in FIG. 6.

A preferred embodiment of the fabric 11 is described by way of example below:

Top bar—70 denier stretch nylon knitting a double needle underlap stitch (2-0, 1-3), with a runner length of 188 inches and an intermediate let off chain;

Middle bar—6 ends out and one end in of a 70 denier yarn having a core of electrically-conductive carbon surrounded by a electrically non-conductive polymer cover stitched according to the sequence:

(8-9, 8-7)×4, (1-0, 1-2)×4, with an intermediate let off pattern chain for the middle bar having a ratio of 1.21 of (O)×1, (4)×23, (O)×1, (4)×23, with a runner length of 90 inches and an intermediate let off chain;

Bottom bar—6 ends out and one end in of a 44 denier untwisted carbon suffused nylon fiber according to the sequence:

(1-0, 1-2)×4, (8-9, 8-7)×4, with an intermediate let off pattern chain for the bottom bar having a ratio of 1.21 of (O)×1, (4)×23, (O)×1, (4)×23, with a runner length of 90 inches.

Machine—Karl Mayer KE-3.

The carbon core with electrically non-conductive polymer cover yarn is sold under the trademark Negastat, originated by DuPont and now owned by William Barnette & Sons, LLC. This yarn has a trilobal cross-section and the cover may comprise either polyester or nylon. Polyester is the preferred fiber.

The carbon suffused nylon yarn is sold by BASF under the trademark Resistat, and is a round cross-section nylon with a surface suffused with carbon.

Application of a fabric made according to this construction to a pain site resulted in prompt and complete relief of the pain during the time of application.

A fabric with pain-relieving characterististics, structures such as garments and bandages constructed therefrom, and related methods are described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A method of reducing endogenous pain by stimulating a flow of endogenous electrical current in the body, and comprising the steps of:
   (a) knitting a stretch fabric comprised of:
      (i) a knit base structure of electrically non-conductive fibers forming courses and wales;
      (ii) a first electrically-conductive carbon fiber knitted into and extending along first selected wales and transversely along first selected courses of the base structure; and
      (iii) a second electrically-conductive carbon fiber knitted into and extending along second selected wales and transversely along second selected courses of the base structure intersecting the first selected courses for contacting the first electrically-conductive carbon fiber and thereby defining a matrix of first and second electrically-conductive carbon fibers that induce an electrical current in the presence of an electrical charge;
   (b) applying the fabric to a pain site; and
   (c) maintaining the fabric on the pain site for the duration of desired relief.

2. A method according to claim 1, wherein the first electrically-conductive carbon fiber is chosen from the group consisting of carbon suffused nylon, filamentary polymer substrates having finely divided, electrically conductive particles embossed on the surface of the surface of the polymer, a core of electrically-conductive carbon surrounded by a electrically non-conductive polymer cover, and graphite fibers, and the second electrically-conductive carbon fiber is chosen from the group consisting of carbon suffused nylon, filamentary polymer substrates having finely divided, electrically conductive particles embossed on the surface of the surface of the polymer, a core of electrically-conductive carbon surrounded by a electrically non-conductive polymer cover, and graphite fibers, but exclusive of the carbon fiber comprising the first electrically-conductive fiber.

3. A method according to claim 1, wherein the first electrically-conductive carbon fiber comprises a carbon suffused nylon and the second electrically-conductive carbon fiber comprises a core of electrically-conductive carbon surrounded by a electrically non-conductive polymer cover.

4. A method according to claim 1, 2 or 3, wherein the matrix contacts both the technical face and technical back of the fabric.

5. A method according to claim 1, 2 or 3 and including the step of fabricating the fabric into a structure selected from the group consisting of garments and bandages.

6. A method according to claim 5, wherein the step of fabricating the fabric comprises the step of fabricating a glove.

7. A method according to claim 5, wherein the step of fabricating the fabric comprises the step of fabricating a glove.

* * * * *